(12) United States Patent
Hazarika et al.

(10) Patent No.: US 10,376,840 B2
(45) Date of Patent: Aug. 13, 2019

(54) **PROCESS FOR EXTRACTION AND SEPARATION OF OXYRESVERATROL FROM *ARTOCARPUS LAKOOCHA* ROXB**

(71) Applicant: Council of Scientific & Industrial Research, New Delhi (IN)

(72) Inventors: Swapnali Hazarika, Assam (IN); Dilip Konwar, Assam (IN); Hirokjyoti Borah, Assam (IN); Somiron Borthakur, Assam (IN); Pranab Barkakati, Assam (IN); Mohan Modon Bora, Assam (IN); Ram Nath Das, Assam (IN)

(73) Assignee: Council of Scientific & Industrial Research, New Delhi (IN)

( * ) Notice: Subject to any disclaimer, the term of this patent is extended or adjusted under 35 U.S.C. 154(b) by 182 days.

(21) Appl. No.: 15/517,439

(22) PCT Filed: Oct. 7, 2015

(86) PCT No.: PCT/IN2015/050129
§ 371 (c)(1),
(2) Date: Apr. 6, 2017

(87) PCT Pub. No.: WO2016/056029
PCT Pub. Date: Apr. 14, 2016

(65) Prior Publication Data
US 2017/0296970 A1    Oct. 19, 2017

(30) Foreign Application Priority Data
Oct. 7, 2014  (IN) ........................ 2853/DEL/2014

(51) Int. Cl.
*B01D 11/02*  (2006.01)
*A61K 36/00*  (2006.01)
(Continued)

(52) U.S. Cl.
CPC ........ *B01D 61/027* (2013.01); *B01D 11/0288* (2013.01); *B01D 23/02* (2013.01);
(Continued)

(58) Field of Classification Search
CPC ...... B01D 61/027; B01D 65/02; B01D 23/02; B01D 71/06; B01D 71/68;
(Continued)

(56) References Cited

U.S. PATENT DOCUMENTS

| 6,528,099 B1* | 3/2003 | Garti | B01D 15/08 |
| | | | 424/725 |
| 7,939,111 B2* | 5/2011 | Cheng | A61K 8/97 |
| | | | 424/725 |

(Continued)

FOREIGN PATENT DOCUMENTS

| CN | 102942455 A | 2/2013 |
| CN | 102219652 B | 4/2013 |
| CN | 103156869 A | 6/2013 |

OTHER PUBLICATIONS

Elisabeth Wenzel et al, "Review Metabolism and bioavailability of trans-resveratol", Mol. Nutr. Food Res., pp. 472-481. (Year: 2005).*

(Continued)

*Primary Examiner* — Joseph W Drodge
(74) *Attorney, Agent, or Firm* — Blank Rome LLP

(57) ABSTRACT

The present invention relates to a process for separation of oxyresveratrol molecule from the extracted solution of *Artocarpus lakoocha* Roxb. through membrane application. The product can be obtained in excellent yield upto 81% in case of extraction using water as solvent and can be separated from the extracted mixture upto 98% using indigenously developed nanofiltration membrane. Only the desired Trans isomer is obtained and no cis isomerization takes place during the extraction process.

8 Claims, 1 Drawing Sheet

(51) Int. Cl.
| | |
|---|---|
| *B01D 61/02* | (2006.01) |
| *B01D 71/06* | (2006.01) |
| *B01D 71/68* | (2006.01) |
| *C07C 37/68* | (2006.01) |
| *B01D 29/00* | (2006.01) |
| *B01D 65/02* | (2006.01) |

(52) U.S. Cl.
  CPC ............ *B01D 65/02* (2013.01); *B01D 71/06* (2013.01); *B01D 71/68* (2013.01); *C07C 37/685* (2013.01); *A61K 36/00* (2013.01); *B01D 2201/202* (2013.01); *B01D 2321/04* (2013.01); *B01D 2321/168* (2013.01)

(58) Field of Classification Search
  CPC .......... B01D 2321/168; B01D 2321/04; B01D 2201/202; B01D 11/02; B01D 11/028; B01D 11/0288; B01D 2311/04; B01D 2311/26; C07C 37/685; A61K 36/00; A61K 2236/30; A61K 2236/31; A61K 2236/51; A61K 2236/53
  USPC .............. 210/634, 636, 639, 644, 650, 651; 424/725; 554/8, 23, 175
  See application file for complete search history.

(56) References Cited

U.S. PATENT DOCUMENTS

| | | | | |
|---|---|---|---|---|
| 2004/0175788 | A1 | 9/2004 | Galaev et al. | |
| 2006/0147556 | A1* | 7/2006 | Brewer | A23L 2/04 424/725 |
| 2012/0094361 | A1 | 4/2012 | Hu et al. | |
| 2013/0001153 | A1* | 1/2013 | Na | B01D 69/125 210/488 |
| 2013/0078698 | A1* | 3/2013 | Lali | C08B 37/0003 435/165 |
| 2014/0099403 | A1* | 4/2014 | Prakash | A23L 2/60 426/61 |
| 2014/0127146 | A1* | 5/2014 | Maes | A61K 8/347 424/59 |
| 2014/0308712 | A1* | 10/2014 | Hanakawa | B01D 61/16 435/99 |

OTHER PUBLICATIONS

Povichit et al., "Antigiycation and Antioxidant Activities of Oxyresveratrol Extracted from the Heartwood of *Artcarpus lakoocha* Roxb", Maejo International Journal of Science and Technology, www.mijst.mju.ac.th; 2010; 4(03); pp. 454-461.

Likhitwitayawuld et al., "A New Dimeric Stilbene with Tyrosinase Inhibitiory Activity from *Artocarpus gomezianus*", Journal of Natural Products, 2001, vol. 64, No. 11, pp. 1457-1459.

Palanuvej et al., "Pharmacognostic Study of *Artocarpus Lakoocha* Heartwood", J. Health Res., www.jhealthres.org/upload/jornal/402/21(4)_p257-262_chanida.pdf; Jan. 1, 2007, pp. 257-262.

Sun., et al., "Efficient Synthesis of Natural Polyphenolic Stilbenes: Resveratrol Piceatannol and Oxyresveratrol", Chemical & Pharmaceutical Bulletin, vol. 58, No. 11, 2010, pp. 1492-1496.

Ti, et al., "Stilbenes and Flavonoids from *Adocarpus nitidus* subsp. *Lingnanensis*", Fitoterapia, www.elsevier.com/locate/fitote; vol. 82, No. 4, 2011, pp. 662-665.

Baruah et al., "Preparation and Characterization of Polysulfone-Cyclodextrin Composite Nanfiltration Membrane: Solvent Effect", Journal of Applied Polymer Science, vol. 25, 2012, pp. 3888-3898.

Adams et al., "Application of Polysulfone/cyclodextrin Mixed-matrix Membranes in the Removal of Natural Organic Matter from Water", Physics and Chemistry of the Earth, vol. 67-69; Dec. 1, 2013; pp. 71-78.

Achour et al., "Concentration of Antioxidant Polyphenols from *Thymus capitatus* Extracts by Membrane Process Technology", Journal of Food Science, vol. 77, No. 6, 2012, pp. C703-C709.

Gautam, et al., "*Artocarpus Lakoocha* Roxb: An Overview", European Journal of Complentary and Alternative Medicine, www.http://mcmed.us/journal/ejcam; Jan. 1, 2014, pp. 10-14.

International Search Report and Written Opinion of PCT/IN2015/050129, dated Jan. 26, 2016, 20 pages.

International Preliminary Report on Patentability, dated Oct. 11, 2016, 8 pages.

Charoenlarp et al. "The Optimus Dose of Puag-Haad in the Treatement of Taeniasis" Journal Article, (abstract only),Feb. 1, 1989, 72(2):71-73.

Charoenlarp et al. "Treatment of Taeniasis with uag-Haad: A Crude Extract of *Artocarpus Lakoocha* Wood", PubMed (abstract only) Dec. 1981; 12(4): 568-70.

Siriboonpipattana et al. "Influence of Extractive methods on Chemical Constituents and Antioxidative Capacity of *Artocarpus lakoocha* Heartwood", J Sci Technol MSU, vol. 27, No. 2, Apr.-Jun. 2008.

Ratanabanaangkoon, et al. "A Preliminary Study on the Antifungal Activity of 2,4,3',5'—Tetrahydroxystilbene on Dermatophytes", J. Sci. Soc. Thailand, 2 (1976), 202-205.

Singhatong et al., Antioxidant and toxicity activities of *Artocarpus lakoocha* Roxb. heartwood extract, Journal of Med. Plants Research vol. 4(1), pp. 947-953, May 18, 2010.

Maneechai et al. "Quantitative Analysis of Oxyresveratrol Content in *Artocarpus lakoocha* and Puag-Haad", Medical Principles and Practice 2009:18:223-227, May 28, 2008.

Suwannalert et al. "Anti-Aging Activity and Non-Toxic Dose of Phytooxyresveratrol from Artocarpus lakoocha Roxb", Tropical Journal of Pharmaceutical Research, Feb. 2012; 11(1): 69-74.

* cited by examiner

PROCESS FOR EXTRACTION AND SEPARATION OF OXYRESVERATROL FROM *ARTOCARPUS LAKOOCHA* ROXB

RELATED APPLICATIONS

This application is a national phase of PCT/IN2015/050129, filed on Oct. 7, 2015, which claims the benefit of Indian Application No. 2853/DEL/2014, filed on Oct. 7, 2014. The content of these applications are hereby incorporated by reference.

FIELD OF THE INVENTION

The present invention relates to a process for the extraction and separation of oxyresveratrol from the heartwood of *Artocarpus lakoocha* Roxb. More particularly, the present invention relates to a process for separation of oxyresveratrol molecule from the extracted solution of *Artocarpus lakoocha* Roxb. through membrane application. Oxyresveratrol is a pharmacologically active compound and has its demand as an anti-aging, antioxidant, cardio-protective, anti-cancer and neuroprotective properties.

BACKGROUND OF THE INVENTION

The plant *Artocarpus lakoocha* Roxb. is a locally available plant in Assam and found plentifully in unreserved forest area. The heartwood of *Artocarpus lakoocha* Roxb. contains varieties of pharmacologically active chemical constituents such as artocarpin, norartocarpin, norcycloartocarpin, resorcinol and oxyresveratrol. Oxyresveratrol (2, 3', 4, 5'-tetrahydroxystilbene) content of it is selected for extraction and separation because of its ever-growing demand as an anti-aging, cardio-protective, anti-cancerous properties besides having its use for treatment of tape-worm infestation. Neuroprotective effects of oxyresveratrol against neurodegradation in Alzheimer's disease has also been referred in recent advances on nutrition and prevention of Alzheimer's disease. However, the selection of appropriate solvent for the extraction of oxyresveratrol from the heartwood of *Artocarpus lakoocha* Roxb. is challenging.

Dilute aqueous mineral acid solution has also been tested for the extraction of oxyresveratrol and it was found that use of dilute aqueous mineral acid had no significant effect on extraction. Extraction in pure water is found to be quite promising for more than 80% w/w extraction of oxyresveratrol from *Artocarpus lakoocha* Roxb. For separation of oxyresveratrol from aqueous solution, membrane technique using indigenously prepared nanofiltration (NF) membrane was used which were characterized by Pore diameter (PMI, Model CCFP-5A), Scanning Electron Microscope (SEM) (LEO 1400VP, UK), Transmission Electron Microscope (TEM) (JEOL, Japan, JEM 2100), IR (PERKIN Elmer System 2000), XRD (JDX-11P-3A, JEOL, Japan), TGA-DTA (Perkin Elmer PC series DSC 7) analysis. The technique has the special advantage because the same extractant which comes out from the membrane cell as feed can be reused.

The oxyresveratrol molecule is recovered from the membrane cell by backwashing the membrane cell with ethanol under a pressure limit within the NF range.

Singhatong S. et al. (Journal of Medicinal Plants Research, 2010, 4(10), 947-953) discloses the antioxidant activity of *Artocarpus lakoocha* heartwood extract, investigated from ethanol extraction by 2,2'-azino-bis(3-ethylbenzthiazoline-6-sulphonic acid) (ABTS) decolorization, 2,2-diphenyl-1-picrylhydrazyl (DPPH) radical and H2O2 scavenging assay. Polyphenolic; total phenolic, flavonoids and tannins were measured. Anti-oxidative stress was studied in AAPH-oxidized blood and glutathione (GSH), and malondialdehyde (MDA) was evaluated. Results showed that antioxidant activities were 128.30±0.13, 55.86±0.01, and 463.49±0.01 μmol Trolox/g extracted from ABTS, DPPH, and H2O2 scavenging methods. One gram of extract contained total phenol (325.63±2.99 mg GE), flavonoids (521.98±0.01 mg QE) and tannins (124.03±0.46 g TE), including rutin and resocinol. In the blood system, a low concentration of extract inhibited MDA progression and improved GSH, which was in contrast to a high concentration with its toxicity effect.

Maneechai S. et al. (Medical Principles and Practice, 2009, 18(3), 223-227) discloses a thin-layer chromatography (TLC) densitometric method for the determination of oxyresveratrol content in *Artocarpus lakoocha* heartwood. The amounts of oxyresveratrol in 3 samples of *A. lakoocha* heartwood collected from its natural habitat were 49.0-182.3 mg/g, whereas those in 11 commercial samples were in the range of 23.4-69.6 mg/g. The Oxyresveratrol contents in 2 samples of traditional drug Puag-Haad were 780.1 and 837.5 mg/g.

Nasapon Povichit et al. (Maejo International Journal of Science and Technology, 2010, 4(03), 454-461) discloses isolation of oxyresveratrol from the heartwood of *Artocarpus lakoocha*, with a yield of 10%. The isolated oxyresveratrol showed strong antiglycation and antioxidant activities. The IC50 value for antiglycation was 2.0±0.03 μg/ml (five times higher than that of aminoguanidine), and the IC50 values for antioxidation were 0.1±0.01 mg/ml (DPPH method) and 0.43±0.03 mg/ml (TBARS method), which were nearly twice as strong as those of resveratrol.

Chanida Palanuvej et al. (J Health Res 2007, 21(4), 257-262) discloses a pharmacognostic study of *Artocarpus lakoocha* heartwood performed on 13 samples collected from five different geographical areas of Thailand. Evaluation of the crude drug was conducted according to the World Health Organization (WHO) guidelines for herbal standardization. Microscopic examination of the powdered drug revealed the presence of parenchyma and fiber cells of the medullary ray, as well as bordered pored tracheids and vessels. The contents of foreign matter, acid-soluble ash, total ash, moisture and oxyresveratrol were determined to be 0.04, 2.06, 2.51, 9.57 and 1.44%, respectively, whereas the ethanol-soluble extractive, water-soluble extractive and loss on drying values were found to be 7.93, 5.27 and 9.79%. In addition, a thin-layer chromatographic system for rapid detection of oxyresveratrol was described, and a method for quantitative analysis of oxyresveratrol content in the crude drug using capillary zone electrophoretic technique was developed.

Kundan Baruah et al. (Journal of Applied Polymer Science, 2012, 125(5), 3888-3898) discloses preparation of α-Cyclodextrin membranes by the phase inversion method using four types of casting solvents such as N-methyl pyrrolidone (NMP), dimethyl sulfoxide (DMSO), dimethyl acetamide (DMAc), and dimethyl formamide (DMF) hereinafter termed as α-CD-NMP, a-CDDMSO, α-CD-DMAc, and a α-CD-DMF, respectively. The membranes were characterized by IR, XRD, TGA-DTA, DSC, and SEM analysis and show that solvents like NMP, DMA, DMF give good uniform morphological membranes and are better than that of DMSO. Thermal decompositions of the pure polymer and composite membranes indicate different range of thermal degradation of the membrane. This study reveals that the casting solvents NMP, DMF, DMAC have nearly same significant effect on morphology and other properties of the membranes. This is explained in terms of demixing behavior of the polymer and the combined effect of solvent volatility and polymer-solvent interactions as estimated from Hansen solubility parameter. Solvent hydrophobicity also affects the performance of the membrane and can be determined in terms of water permeability.

P Suwannalert et al. (Tropical Journal of Pharmaceutical Research, 2012, 11 (1), 69-74) discloses a study of anti-aging activity and toxicity doses of phytooxyresveratrol extracted from *Artocarpus lakoocha* Roxb. *Artocarpus lakoocha* 100 g was extracted with 2 ml of 95% ethanol to obtain phytooxyresveratrol (POV). Total phenolic content, as well as free radical scavenging and anti-glycation activities of POV were characterized in order to assess its anti-aging properties. The models of DNA nicking and bacterial reverse mutation (Ames) were applied to the extract in order to determine its effective and toxic doses, respectively.

Pranee Siriboonpipattana et al. (Journal of Science Technology Mahasarakham University, 2008, 27(2), 100-109) discloses that phytoalexin have been reported in a genus *Artocarpus*. Analytical methods for measuring resveratrol and resorcinol in *Artocarpus lakoocha* heartwood extracts were adapted to isolate with several methods (distill extract, aqueous extract, methanolic extract and methanolic extract in a Soxhlet extractor), and analyzed by reversed phase HPLC using a C-18 column. Total phenolic content was determined spectrophotometrically with phenol Folin-Ciocalteauûs reagent, and antioxidative capacity employing the 1,1-diphenyl-2-picrylhydrazyl stable free radical (DPPH).

Liu Zhichang et al. (Shizhen Guoyi Guoyao, 2009, 20(1), 203-204) discloses the membrane separation. technology used in the purification of resveratrol and reducing pollution were. After liquid state fermentation, resveratrol was extracted by 60% ethanol at room temperature, solid/liquid ratio 1:8, the filtrate was obtained by filtering, and dealt it with two membrane equipments, the purity of resveratrol was detected by HPLC. The purity of resveratrol reached 30.5% after the microfiltration membrane, and after the ultrafiltration membrane the purity of resveratrol could reach 55.8%. This method can reduce the cost of production without toxic and harmful solvents and it can realize clean production.

CN102219652 discloses about a method for preparing water-soluble resveratrol from giant knotweed rhizome. Specifically, giant knotweed rhizome as the raw material is subjected to a healing treatment, pulverization and fermentation, and then extracted by methylal. The extract generated then undergoes condensation, membrane separation, macroporous resin adsorption and elution. And the eluate obtained is condensed, recrystallized and dried in vacuum, thus obtaining resveratrol. Next, by the preparation method of chitosan nanoparticles, water-soluble resveratrol can be obtained. A product prepared with the method of the invention is of high purity which is up to more than 98%, low production cost that is 20-30% lower than traditional methods, and high yield about 8-10% higher than traditional methods. The method is also effective in increasing the solubility and oral bioavailability of resveratrol. According to the method of the invention, clean production and pollution-free purifying processes are realized, and the solvent therein is recyclable.

CN103156869 discloses about extraction of sanggenone C and sanggenone D from white mulberry root-barks, mulberry twigs and folium leaves and a new medicine application of a composition comprising the sanggenone C and the sanggenone D which are main ingredients, particularly the application of the single ingredient sanggenone C or sanggenone D and the composition composed of the sanggenone C, the sanggenone D, mulberrin, mulberroside, oxidized resveratrol, resveratrol and deoxynojirimycin in preparation of alpha-glucosidase inhibitor medicines. The composition is prepared by respectively extracting medicinal materials containing the chemical components above and blending according to certain proportions, or using several extraction methods for extracting the medicinal materials simultaneously containing the chemical components above. The white mulberry root-barks, the mulberry twigs and the folium leaves are accidentally found to contain the sanggenone C and the sanggenone D apart from containing alkaloids such as deoxynojirimycin; and the sanggenone C and the sanggenone D have stronger pharmacological activity than the alkaloids such as deoxynojirimycin.

CN102942455 discloses a method for extracting oxyresveratrol from mulberry branches. The mulberry branches are used as raw materials. The method includes the following steps: (1) the mulberry branches are extracted, concentrated and dried by using an alcohol-water solution with 65%-75% alcohol volume content, and a crude extract is obtained; (2) degreasing treatment is performed on the crude extract by using petroleum ether, ethyl acetate is used for performing multiple extraction, ethyl acetate extract liquid is combined, a solvent is recovered through vacuum decomposition, a fluid substance is obtained, the fluid substance is dried in vacuum at the temperature of 40 DEG C. to obtain a semi-finished product; and (3) the semi-finished product obtained in the step (2) is dissolved totally through an ethanol-water solution and mixed with macroporous resin D101, absorption is performed fully, a column is arranged, the ethanol-water solution is used as eluant to perform gradient elution or isocratic segmentation elution, the eluant is collected, concentrated and dried, and recrystallization is performed through a mixed solvent of acetone and petroleum ether to obtain oxyresveratrol crystals. The method can extract oxyresveratrol from the mulberry branches effectively, is simple to operate, low in cost and suitable for large-scale production.

US2004175788 discloses a method for the separation of at least one low molecular weight bioproduct from a cell culture mixture comprising uni-cellular organisms, broth and said at least one bioproduct by passing said cell culture mixture through a bed of an adsorbent material to adsorb said at least one bioproduct on said adsorbent material whereas said unicellular organisms and said broth are passing through said bed, whereafter the adsorbed bioproduct or bioproducts is/are eluted from said bed of adsorbent material, wherein said adsorbent material on its surface is provided with a material capable of preventing non-specific adsorption of said unicellular organisms to said adsorbent material.

US2012094361 discloses a cross-flow membrane filtration method for the removal or separation of algal cells from an aqueous environment. The methods of the invention may be used for the simultaneous algal harvesting/dewatering and water/wastewater purification and recycling.

Charoenlarp P et al. (Journal of the Medical Association of Thailand, 1989, 72(2), 71-73) discloses the optimum dose of Puag-Haad in the treatment of *taeniasis*. In this work, Forty-two percent of 24 patients with *Taeniasis saginata* were cured by two-gram dose of a crude aqueous extract of the wood *Artocarpus lakoocha*, Puag-Haad, while eighty percent of 25 patients were cured by three-gram dose which is comparable to the results of five-gram dose but had less side-effect. Thus, the three-gram dose of Puag-Haad is recommended in the treatment of *taeniasis*.

Charoenlarp P et al. (Southeast Asian J Trop Med Public Health, 1981, 12(4), 568-70) discloses about a treatment of *taeniasis* with Puag-Haad: a crude extract of *Artocarpus lakoocha* wood. In this work, thirty-nine patients with tapeworm infection were treated with five grams of crude aqueous extract of *Artocarpus lakoocha* wood, "Puag-Haad". Seven of them vomited the drug immediately. Of the 32 patients, segments with scolices of *Taenia saginata* and of *Taenia solium* were recovered from 24 and 2 patients respectively. The side effects were vomiting and nausea.

Ratanabanangkoon K. et al. (J. Sci. Soc. Thailand, 1976, 2, 202-205), discloses that 2,4,3',5'-Tetrahydroxystilbene inhibits the growth of *Trichophyton rubum, Trichophyton mentagrophytes, Trichophyton tonsurans, Microsporum canis, Microsporum gypseum* and *Epidermophyton floccosum*. The minimal inhibitory concentration was 2.0 mM in all cases. It is inactive against *Candida albicans*.

OBJECTIVE OF THE INVENTION

The main objective of the present invention is to provide a novel process for extraction and separation of oxyresveratrol from the heartwood extract of *Artocarpus lakoocha* Roxb.

Another objective of the process is to provide a greener approach for extraction of oxyresveratrol using water as an extractant. Also, for extraction of oxyresveratrol different common solvents such as alcohols, aqueous mineral acids and water are used for selecting the best solvent.

Yet another objective of the process is to provide a novel separation technique wherein membrane technology is used which is a less energy intensive, cost effective and eco-friendly process of separation.

SUMMARY OF THE INVENTION

The present invention discloses a process for preparation of oxyresveratrol from heartwood of *Artocarpus lakoocha* Roxb., said process comprising the steps of:

(i) mixing of *Artocarpus lakoocha* Roxb. powder with water at a temperature in the range of 30° C.-70° C. for 4 to 10 hours and filtering to obtain a solution of the extract (ii) subjecting the solution of the extract obtained in step (i) to membrane treatment in a two compartment membrane cell containing a nanofiltration membrane selected from Alpha cyclodextrin-polysulfone composite nanofiltration-membrane, Beta cyclodextrin-polysulfone composite nanofiltration membrane or Gama cyclodextrin-polysulfone composite nanofiltration membrane by circulating through the nanofiltration membrane using a peristaltic pump at a flow rate in the range of 42.50 ml/min to 107.14 ml/min; and (iii) collecting oxyresveratrol from the feed side of membrane.

Accordingly the present invention provides a process for extraction and separation of oxyresveratrol by using water as extracting solvent. In an embodiment of the invention, water is selected as the best extracting agent in comparison to the other solvents used. The other solvents used are aqueous mixture of mineral acids such as Hydrochloric acid and Sulphuric acid. In another embodiment of the invention methanol and ethanol are used as extracting solvent. In an embodiment of the invention, the effect of temperature on the extraction of oxyresveratrol is studied in the range of 30° C. to 70° C. and optimum temperature is found to be 50° C. for extraction of oxyresveratrol using water as solvent. In another embodiment of the invention, the effect of time on the extraction of oxyresveratrol is studied in the range of 1 hr to 10 hrs and the optimum extraction time for extraction of oxyresveratrol using water as solvent is found to be 4 hours. The present invention relates to a process for separation of oxyresveratrol from the extractant using membrane technology. The membranes used for the separation process are alpha, beta and gamma cyclodextrin composite with polysulfone. In another embodiment of the invention, the water used for extraction is deionized water produced in Milli-Q system. In one embodiment of the invention the separation experiment is carried out in a disproportionate two-compartment membrane cell whose compartment volumes on the feed and permeate side are 150 and 120 ml respectively. The polymeric membrane is placed between the compartments with silicone-rubber packing and the cell is connected with a reservoir of 500 ml capacity. The solutions of the extracted compound in aqueous phase is stirred continuously and circulated through the membrane by using a peristaltic pump at the flow rate range of 42.50 ml/min to 107.14 ml/min. The area of the membrane is 19.6 cm$^2$ and the trans membrane pressure of the experiment is in the range of 11.3 psi (77910.76 Pa) to 18.3 psi (126174.1 Pa). The sample solutions are collected at an interval of one hour for seven hours from the feed side and analyzed by UV and HPLC.

The present invention also relates to process for the extraction and separation of oxyresveratrol from heartwood of *Artocarpus lakoocha* Roxb. using water as extracting solvent and membrane technology as separation technique. The said process comprises the mixing of *Artocarpus lakoocha* Roxb. powder with warm water at 50° C. for 4 hours, filtration of the powder through filter paper and filtrate is subjected to membrane treatment in a two compartment membrane cell containing beta-cyclodextrine-polysulfone composite nanofiltration membrane for separation of the product. The membrane can be reused for several cycles with consistent activity by backwashing the membrane with ethanol. The isolated oxyresveratrol shows strong antiglycation and antioxidant activities. From oxyresveratrol (trans-2,4,3',5'-tetrahydroxystilbene) several derivatives including trans-2-methoxy-4,3',5'-trihydroxystilbene, trans-2,3'-dimethoxy-4,5'-dihydroxystilbene, trans-4,3'-dimethoxy-2,5'-dihydroxystilbene, trans-2,4,3',5'-tetramethoxystilbene, cis-2,4,3',5'-tetramethoxystilbene, 2,4,3',5'-tetrahydroxybibenzyl and 2,4,3',5'-tetramethoxybibenzyl can be synthesized. Oxyresveratrol present in the *Artocarus lakoocha* Roxb. stem can be used as vermifuge for treatment of tape-worm infestation and the product has evergrowing interest of anti-aging, cardioprotective and anticancerous properties. The product has strong antioxidant activity because of the presence of flavonoids and phenolic compounds. The product has marked anthelmintic effect than standard drugs. The product has also neuroprotective effects against neurodegeneration in Alzheimer's disease.

DETAILED DESCRIPTION OF THE INVENTION

Figure 1:
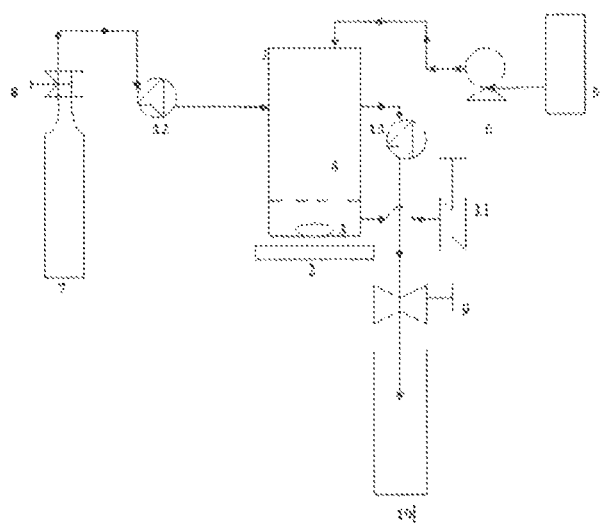
FIG. 1: Flow diagram of permeation experiment the whereas the parts are as following
1. Membrane cell
2. Magnetic stirrer
3. Magnetic capsule
4. Membrane
5. Feed tank
6. Peristaltic pump
7. N$_2$ gas 8. Gas valve
9. Gas valve
10. Water vessel
11. Sample collecting valve
12. Pressure gauze
13. Pressure gauze
Figure 2:
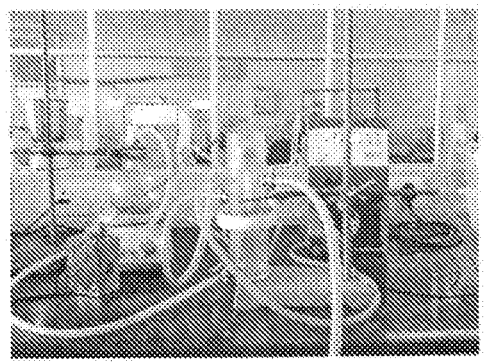
FIG. 2: Experimental set up of separation experiment

The biological material i.e. *Artocarpus lakoocha* Roxb. used for the process of the present invention is procured from Area: Kakojan P. O. Kakojan Pin code: 785107, Assam, India.

The present invention relates to process for the extraction and separation of oxyresveratrol from heartwood of *Artocarpus lakoocha* Roxb. using water as extracting solvent and membrane technology as separation technique. In the process, water is selected as the best extracting agent in comparison to the other solvents used. The said process comprises the mixing of *Artocarpus lakoocha* Roxb. powder with warm water at 50° C. for 4 hours, filtration of the powder through filter paper. For separation of oxyresveratrol from the extractant, the filtrate is subjected to membrane treatment in a two compartment membrane cell containing beta-cyclodextrine-polysulfone composite nanofiltration membrane for separation of the product. The membrane is reusable for several cycles with consistent activity by backwashing with ethanol.

The membranes used for the separation process is beta cyclodextrin composite with polysulfone. The polysolfone-beta cyclodextrin (PS-CD) composite membranes are prepared indigenously using phase inversion technique. The separation experiment is carried out in a disproportionate two-compartment membrane cell whose compartment volumes on the feed side and permeate side are 150 and 120 ml respectively. The polymeric membrane is placed between the compartments with silicone-rubber packing and the cell is connected with a reservoir of 500 ml capacity. The solutions of the extracted compound of concentration in the range 0.64 mmolL$^{-1}$ to 0.76 mmolL$^{-1}$ in aqueous phase is stirred continuously and circulated through the membrane by using a peristaltic pump at the flow rate range of 42.50 ml/min to 107.14 ml/min. The area of the membrane is 19.6 cm$^2$ and the trans membrane pressure of the experiment is in the range of 7.2 psi (49642.3 Pa) to 21.75 psi (149960.97 Pa). The sample solutions are collected at an interval of one hour for seven hours from the feed side and analyzed by UV and HPLC.

EXAMPLES

Example 1: Extraction of Oxyresveratrol (General Method)

10 gm of heart wood of *Artocarpus lakoocha* Roxb. is stirred continuously with different solvent such as water, methanol, ethanol, aqueous H$_2$SO$_4$ and aqueous HCl at 30° C. to 70° C. for 10 hours. The samples are collected at a regular interval of time and filtered. The filtrate is analyzed for the presence of oxyresveratrol by UV visible spectrophotometer. The absorbance peak of oxyresveratrol is obtained at 329 nm. The concentration of oxyresveratrol is calculated using the calibration curve.

Example 2: Optimization of the Procedure

From the extraction method given in Example 1 following results have been obtained

TABLE 1

Extraction of oxyresveratrol at different time in water
Ratio of wood and solvent: 1:15
Temperature: 50° C.

| Sl. No. | Time (hour) | % of extraction |
|---|---|---|
| 1 | 1 | 17.79 |
| 2 | 2 | 53.70 |
| 3 | 3 | 71.43 |
| 4 | 4 | 81.49 |
| 5 | 5 | 79.70 |
| 6 | 6 | 66.60 |
| 7 | 7 | 43.89 |
| 8 | 8 | 32.90 |
| 9 | 9 | 22.57 |
| 10 | 10 | 13.09 |

TABLE 2

Extraction of oxyresveratrol in different solvents and temperatures
Ratio of wood and solvent: 1:15
Time: 4 hours

| | | % of extraction | | |
|---|---|---|---|---|
| Sl. No. | Solvent | 30° C. | 50° C. | 70° C. |
| 1 | H$_2$O | 38.65 | 81.49 | 44.93 |
| 2 | Methanol | 19.20 | 20.0 | 15.54 |
| 3 | Ethanol | 23.00 | 25.96 | 18.21 |
| 4 | Sulphuric acid (aq.) | 5.52 | 6.21 | 2.25 |
| 5 | Hydrochloric acid (aq.) | 6.25 | 8.00 | 3.29 |

TABLE 3

Extraction of oxyresveratrol at different ratio of wood and solvent
Solvent: Water, Temperature: 50° C., Time: 4 hours

| Sl. No. | Ratio of wood and solvent (w/w) | % of extraction |
|---|---|---|
| 1 | 1:30 | 30.85 |
| 2 | 1:25 | 28.25 |
| 2 | 1:20 | 42.45 |
| 3 | 1:15 | 81.49 |
| 4 | 1:10 | 42.55 |

TABLE 4

Separation of oxyresveratrol by membrane
Concentration of feed = 0.76 mmolL$^{-1}$,
Pressure = 14.50 psi (99973.98 Pa)

| Membrane | Flow rate (ml/min) | Flux (mmol m$^{-1}$h$^{-1}$) | % of recovery |
|---|---|---|---|
| Alpha cyclodextrin-polysulfone composite NF membrane | 107.14 | 8.81 | 88.86 |
| | 75 | 8.17 | 83.42 |
| | 42.85 | 5.89 | 56.62 |
| Beta cyclodextrin-polysulfone composite NF membrane | 107.14 | 9.88 | 98.07 |
| | 75 | 9.84 | 97.64 |
| | 42.85 | 9.08 | 91.26 |
| Gama cyclodextrin-polysulfone composite NF membrane | 107.14 | 5.01 | 50.10 |
| | 75 | 4.59 | 41.12 |
| | 42.85 | 4.02 | 32.54 |

TABLE 5

Separation of oxyresveratrol by membrane
Concentration of feed = 0.76 mmolL$^{-1}$, Flow rate = 107.14 ml/min

| Membrane | Pressure (psi) | Pressure (Pa) | Flux (mmol m$^{-1}$h$^{-1}$) | % of recovery |
|---|---|---|---|---|
| Alpha cyclodextrin-polysulfone composite NF membrane | 7.20 | 49642.3 | 5.81 | 63.18 |
|  | 14.50 | 99973.98 | 8.81 | 88.86 |
|  | 21.75 | 149960.97 | 9.02 | 90.69 |
| Beta cyclodextrin-polysulfone composite NF membrane | 7.20 | 49642.3 | 5.81 | 64.43 |
|  | 14.50 | 99973.98 | 9.88 | 98.07 |
|  | 21.75 | 149960.97 | 7.65 | 55.78 |
| Gama cyclodextrin-polysulfone composite NF membrane | 7.20 | 49642.3 | 3.24 | 35.30 |
|  | 14.50 | 99973.98 | 5.01 | 50.10 |
|  | 21.75 | 149960.97 | 4.23 | 42.25 |

TABLE 6

Separation of oxyresveratrol by membrane
Pressure = 14.50 psi (99973.98 Pa), Flow rate = 107.14 ml/min

| Membrane | Concentration (mmolL$^{-1}$) | Flux (mmol m$^{-1}$h$^{-1}$) | % Recovery |
|---|---|---|---|
| Alpha cyclodextrin-polysulfone composite NF membrane | 0.76 | 5.89 | 88.86 |
|  | 0.69 | 5.21 | 56.28 |
|  | 0.64 | 4.60 | 54.27 |
| Beta cyclodextrin-polysulfone composite NF membrane | 0.76 | 9.88 | 98.07 |
|  | 0.69 | 8.78 | 92.56 |
|  | 0.64 | 7.98 | 88.64 |
| Gama cyclodextrin-polysulfone composite NF membrane | 0.76 | 5.01 | 50.01 |
|  | 0.69 | 3.21 | 43.65 |
|  | 0.64 | 3.11 | 42.11 |

The Main Advantages of the Present Invention are:
1. The method is very simple and environmentally benign.
2. The product can be obtained in excellent yield upto 81% in case of extraction using water as solvent.
3. The product can be separated from the extracted mixture upto 98% using indigenously developed nanofiltration membrane.
4. Only the desired trans isomer is obtained and no cis isomerisation takes place during the extraction process.
5. The oxyresveratrol molecule is easily recoverable from the membrane cell by backwashing with ethanol under a pressure limit within the NF range.
6. The process is continuous and recyclable.
7. The membrane can be reused for consecutively more than ten times for separation of oxyresveratrol without any loss in activity of the membrane. Also, there is no generation of any toxic chemical waste to the environment making the process simple, green, environmentally benign, economically viable and less energy intensive.

OTHER RELATED REFERENCES

1. J. of Planar Chromatography 24(2011) 2, 125-129
2. Chem. Pharm. Bull. 58 (11) 1492 (2010)
3. Brajilian journal of Pharmacology, 123, 1691 (1998)
4. Brain Research, 1017, 98 (2004)
5. Journal of Biological Chemistry, 277(18), 16340 (2002)
6. US Patent No. 20040175788A1 (2004)
7. US 20120094361A1 (2012)
8. J. Applied Polymer Science, 125(5), 3388-3898, (2012)
9. CN101591680-B, Method for extracting oxidized resveratrol
10. CN101591680-A; CN101591680-B
11. Chemistry & Biodiversity, 2006, 3, 1138-1143
12. Phytochemistry, 2012, 81, 42-49
13. Pak. J. Pharm. Sci., 2010, 23(4), 403-408
14. Journal of Natural Products, 2001, 64(11), 1457-1459
15. Medicinal Principles and Practice, 2009: 18: 223-227

We claim:

1. A process for extraction and separation of oxyresveratrol from heartwood of *Artocarpus lakoocha* Roxb., said process comprising the steps of:
   (i) mixing *Artocarpus lakoocha* Roxb. Powder obtained from the heartwood with water at a temperature in the range of 30° C.-70° C. for 1 to 10 hours to extract a solution and filtering the solution to obtain a solution enriched in oxyresveratrol;
   (ii) subjecting the solution enriched in oxyresveratrol obtained in step (i) to a membrane treatment in a two compartment membrane cell containing a nanofiltration membrane selected from an Alpha cyclodextrin-polysulfone composite nanofiltration membrane, a Beta cyclodextrin-polysulfone composite nanofiltration membrane or a Gamma cyclodextrin-polysulfone composite nanofiltration membrane by circulating through the nanofiltration membrane with a peristaltic pump at a flow rate in the range of 42.50 ml/min to 107.14 ml/min to obtain oxyresveratrol; and
   (iii) collecting the oxyresveratrol obtained in step (ii) from feed side of the membrane;
      wherein the trans membrane pressure across the membrane in step (ii) is maintained within the range of 7.2 psi to 21.75 psi.

2. The process as claimed in claim 1, wherein the mixing of *Artocarpus lakoocha* Roxb. powder with water is done at 50° C.

3. The process as claimed in claim 1, wherein the mixing of *Artocarpus lakoocha* Roxb. powder with water is done for 4 hours.

4. The process as claimed in claim 1, wherein the nanofiltration membrane is a beta cyclodextrin-polysulfone composite nanofiltration membrane.

5. The process as claimed in claim 1, wherein the two compartment membrane cell has a feed side and a permeate side with volumes of 150 ml and 120 ml respectively.

6. The process as claimed in claim 1, wherein the trans membrane pressure across the membrane is maintained at 14.50 psi.

7. The process as claimed in claim 1, wherein the membrane is cyclically backwashed with ethanol.

8. The process as claimed in claim 1, wherein the oxyresveratrol obtained is a trans isomer of oxyresveratrol.

* * * * *